US00PP28224P3

(12) United States Plant Patent
Van Dijk

(10) Patent No.: US PP28,224 P3
(45) Date of Patent: Jul. 25, 2017

(54) ***ANTHURIUM* PLANT NAMED 'ANTHDASYM'**

(50) Latin Name: ***Anthurium andreanum* L.**
Varietal Denomination: ANTHDASYM

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 90 days.

(21) Appl. No.: 14/757,114

(22) Filed: Nov. 20, 2015

(65) Prior Publication Data

US 2017/0150672 P1 May 25, 2017

(51) Int. Cl.
*A01H 5/02* (2006.01)

(52) U.S. Cl.
USPC ..... Plt./369

(58) Field of Classification Search
USPC ..... Plt./369
See application file for complete search history.

(56) References Cited

PUBLICATIONS

UPOV hit on *Anthurium* plant named 'ANTHDASYM', QZ PBR 41008, published Oct. 15, 2013.*
UPOV hit on *Anthurium* plant named 'ANTHDASYM', MX PBR 1526, published Oct. 20, 2015.*

* cited by examiner

*Primary Examiner* — Anne Grunberg
(74) *Attorney, Agent, or Firm* — Jondle & Associates, P.C.

(57) ABSTRACT

A new and distinct variety of *Anthurium* plant named 'ANTHDASYM' particularly distinguished by having dark red, heart-shaped, cupped and very durable spathes that retain the original color for very long periods of time, green, long cordate, durable leaves, rich shoot formation, rich flowering continuously throughout the year, a compact and full plant habit and a plant height of 30 cm to 35 cm, is disclosed.

3 Drawing Sheets

Genus and species: *Anthurium andreanum* L.
Variety denomination: 'ANTHDASYM'.

BACKGROUND OF THE NEW PLANT

The present invention comprises a new and distinct variety of *Anthurium*, botanically known as *Anthurium andreanum* L., and hereinafter referred to by the variety name 'ANTHDASYM'. The new variety originated from a hybridization made in December 2006 in Bleiswijk, The Netherlands. The female parent was a red *Anthurium* pot plant designated '8477-02' (unpatented), and the male parent was a red *Anthurium* plant designated '9863-02' (unpatented).

A single plant was selected in April 2008 and has been asexually reproduced repeatedly by tissue culture in Bleiswijk, The Netherlands over a seven-year period. The present invention has been found to retain its distinctive characteristics through successive asexual propagations.

Plant Breeder's Rights for this variety have been applied for in the European Union on Jul. 5, 2013 and in Mexico on Aug. 4, 2015. 'ANTHDASYM' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Large bright red cordate spathe;
2) Short white spadix with yellow-green tip;
3) Compact plant habit with some shoots; and
4) Dark green, long cordate leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 35-week old plant grown in a greenhouse in Bleiswijk, The Netherlands in July 2015.

DESCRIPTION OF THE NEW VARIETY

Figure 1:
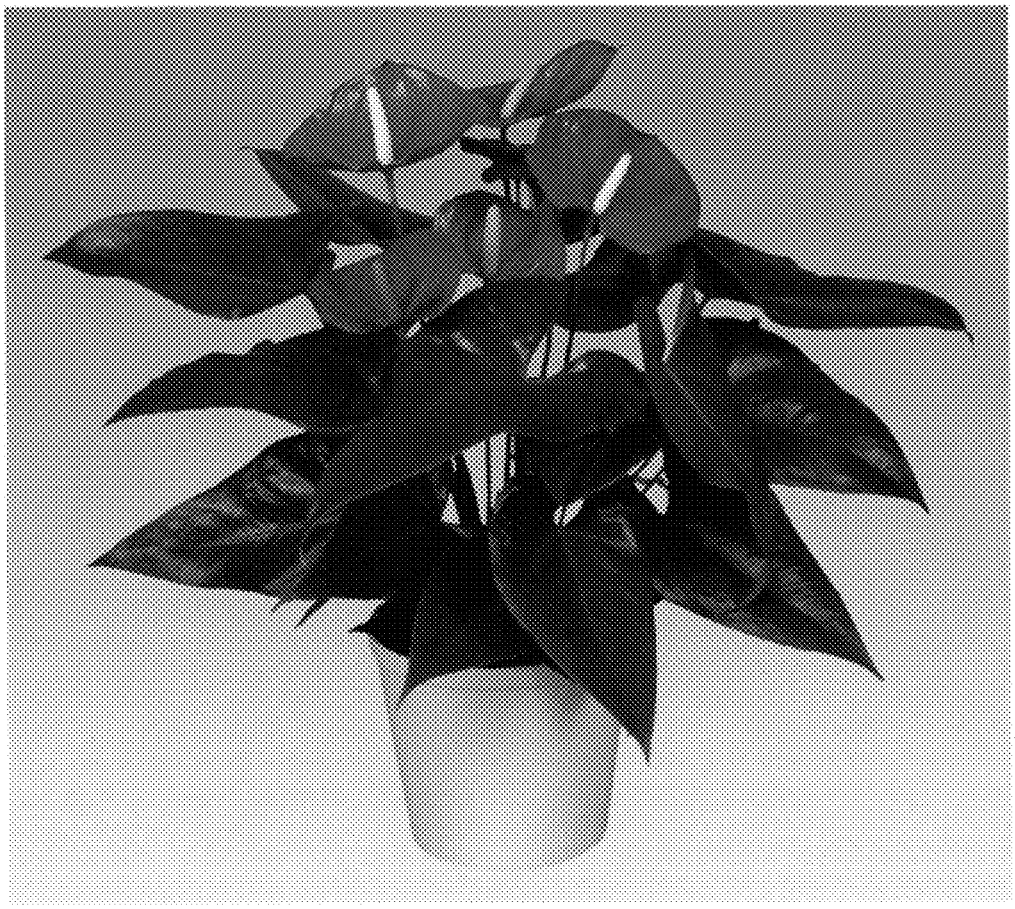
FIG. 1 shows the overall plant habit, including blooms and foliage.
Figure 2:
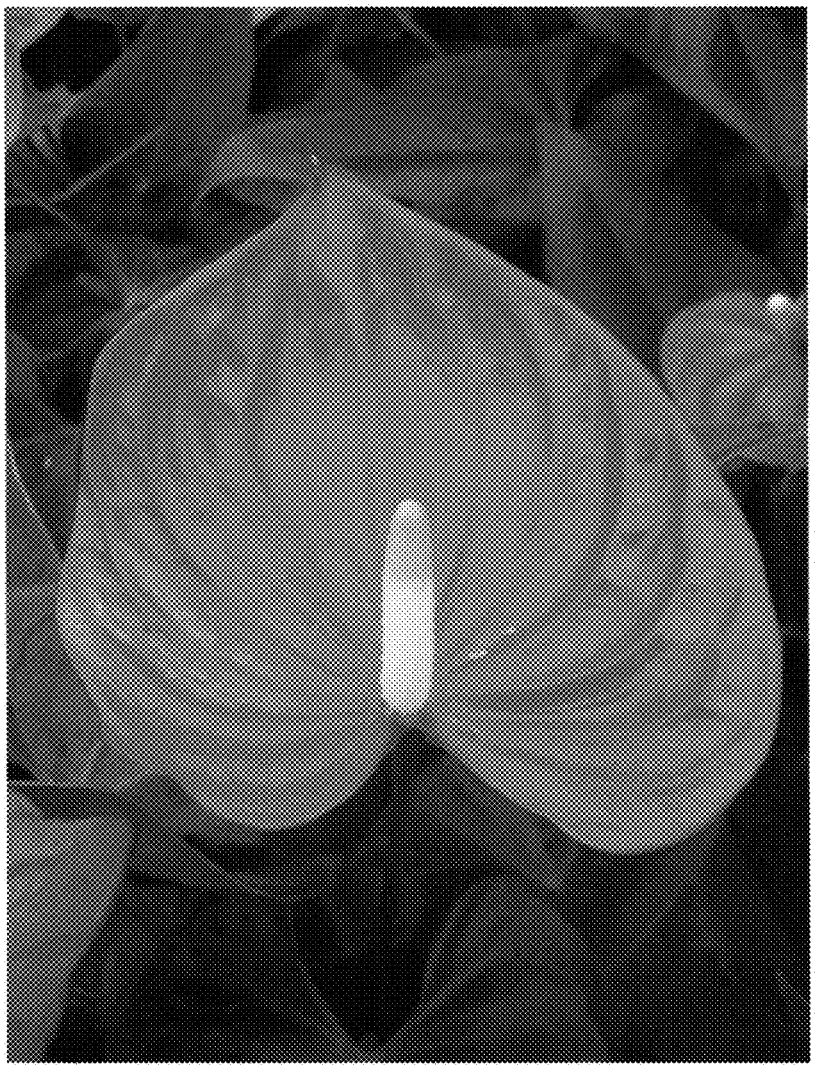
FIG. 2 shows a close-up of the mature spathe.
Figure 3:
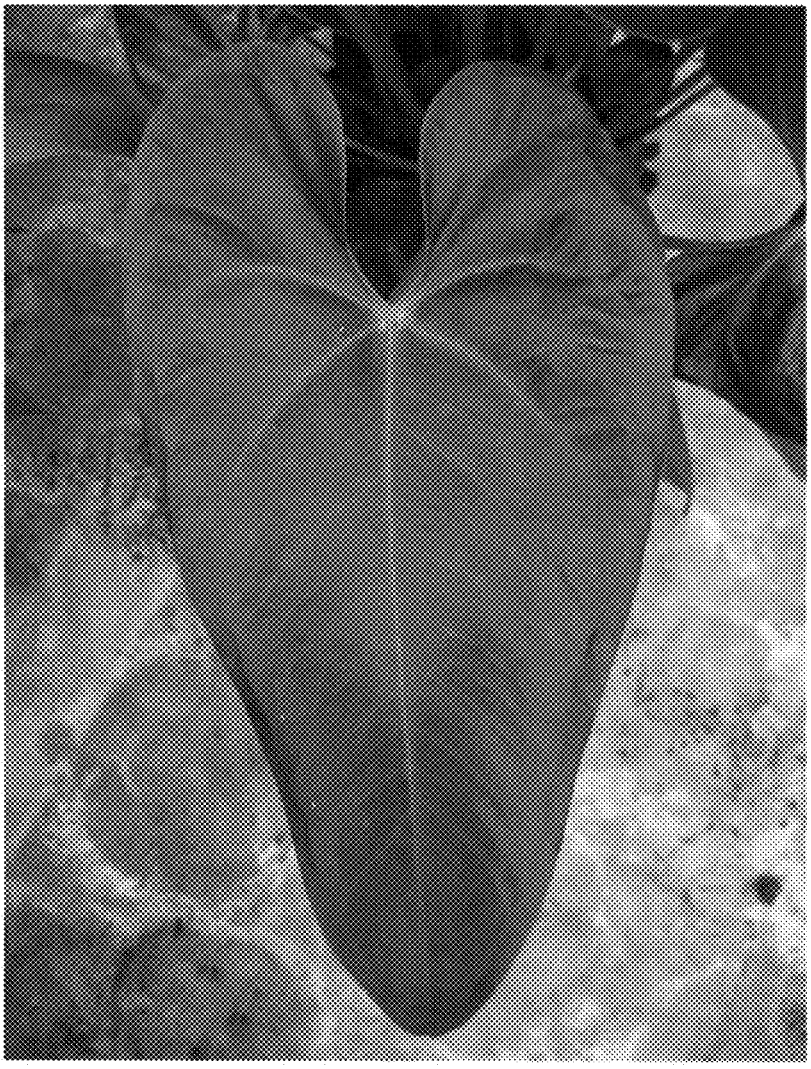
FIG. 3 shows the upper leaf blade surface.

The following detailed description sets forth the distinctive characteristics of 'ANTHDASYM'. The data which define these characteristics were collected from asexual reproductions carried out in Bleiswijk, The Netherlands. The plant history was taken on 35-week old plants which were planted from tissue culture in 14-centimeter pots and grown in a glass greenhouse between 19° C. and 24° C. Observations were made in July 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDASYM'.

Parentage:

*Female parent*.—*Anthurium* plant '8477-02' (unpatented).

*Male parent*.—*Anthurium* plant '9863-02' (unpatented).

Plant:

*Propagation*.—Tissue culture.

*Root description*.—Fleshy light pink-white colored roots with small hairy lateral roots having yellow-colored root tips.

*Time to produce a finished flowering plant*.—32 to 37 weeks for a 14 cm pot.

*Growth habit*.—Herbaceous perennial.

*Height* (*measured from soil, including inflorescence*).—30.0 cm to 35.0 cm.

*Width* (*measured from leaf tips*).—35.0 cm to 40.0 cm.

Leaves:

*Immature leaves*.—Length: 14.0 cm to 18.0 cm. Width: 7.0 cm to 10.0 cm. Color: Upper surface: RHS 146A. Lower surface: RHS 148A. Texture (both upper and lower surfaces): Shiny.

*Mature leaves*.—Length (fully expanded): 17.0 cm to 20.0 cm. Width: 9.0 cm to 12.0 cm. Shape: Long cordate. Apex: Narrow acuminate. Base: Cordate. Leaf blade angle with the petiole: Between 110 degrees and 130 degrees. Leaf margin: Entire. Color: Upper surface: RHS 147A. Lower surface: RHS 147B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Arrangement: Leaf blade has two lobes extending past the petiole. The lobes are non-touching. Length of lobes of mature leaf blades: 3.0 cm to 4.5 cm. Width of lobes of mature leaf blades: 3.5 cm to 4.5 cm. Distance for petiole/leaf junction to highest point on lobes of mature leaf blades: 2.0 cm to 2.5 cm.

*Petiole*.—Cross-section: Round. Diameter: 0.3 cm to 0.4 cm. Length: 12.0 cm to 22.0 cm for a mature leaf size. Color: Mature leaf: RHS 146B. Immature leaf: RHS 146C. Cataphyll color surrounding the petiole: Outside: RHS 174B. Inside: RHS 182C-D.

*Geniculum*.—Length: 2.0 cm to 3.0 cm. Width: 0.35 cm to 0.45 cm. Color: RHS 146A.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Over a year.

*Longevity of the flower as a cut flower*.—30 to 35 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 100 degrees and 110 degrees; the spathe stands on a wiry peduncle about 3.0 cm to 5.0 cm above the foliage.

*Shape*.—Cordate.

*Apex*.—Acuminate.

*Base*.—Cordate.

*Texture*.—Shiny and slightly blistered.

*Margin*.—Entire.

*Size*.—Height (peduncle length at maturity): 12.0 cm to 22.0 cm. Length: 7.0 cm to 11.0 cm. Width: 7.0 cm to 11.0 cm.

*Lobes*.—Arrangement: The spathe has two lobes extending past the peduncle. The lobes are non-touching. Length: 1.5 cm to 2.5 cm. Width: 3.0 cm to 5.0 cm.

*Color*.—Just fully open: Upper surface: RHS 46A. Lower surface: RHS 45A. This red color remains for a very long period, at least more than 30 weeks after opening.

Peduncle:

*Shape*.—Erect.

*Cross-section*.—Round.

*Length*.—15.0 cm to 25.0 cm.

*Diameter*.—0.3 cm to 0.45 cm.

*Color*.—RHS 144A.

Flowering time:

*General*.—One small rooted untreated tissue culture plant of 8.0 cm tall will flower after 7 to 8 months, depending on the season, and 5 to 7 blossoms appear. More blossoms appear after some additional weeks so that a full flowering and commercial plant will have 7 to 9 red spathes. Smaller blossoms may occur on less mature plants.

Spadix:

*Size*.—Length: 3.0 cm to 4.0 cm (depending on flower size). Width (at apex): 0.5 cm to 0.6 cm. Width (at base): 0.8 cm to 0.9 cm.

*Shape*.—Columnar.

*Angle from spadix tip to peduncle*.—160 to 170 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 153A-B. Mature: RHS 158B. Aged: RHS 151A-B.

Flowers:

*Quantity per spadix*.—180 to 230.

*Spadix flower arrangement*.—Bisexual, rounded in cross-section.

*Shape*.—Rounded.

*Size*.—Length: 0.05 cm to 0.1 cm. Diameter (maximum): 0.1 cm.

*Color*.—RHS 156D.

Reproductive organs:

*Stamens*.—Not visible.

*Pollen amount*.—Very few.

*Pollen color*.—RHS 156D.
*Pistil*.—Quantity: Many. Length: Less than 0.01 cm. Color: RHS 156D.
*Style*.—Not observed.
*Stigma*.—Shape: Ovoid. Diameter: Less than 0.01 cm. Color: RHS 156D.
*Ovary*.—Rarely visible.
*Ovary color*.—Not measured.
Fruit and seed set: None observed.

COMPARISON WITH PARENTAL AND COMMERCIAL VARIETIES

'ANTHDASYM' differs from the female parent plant '8477-02' (unpatented) in that 'ANTHDASYM' has a light green leaf color, whereas '8477-02' has a more dark green leaf color. Additionally, 'ANTHDASYM' has a shorter spadix than '8477-02'.

'ANTHDASYM' differs from male parent plant '9863-02' (unpatented) in that 'ANTHDASYM' has a dark red spathe, whereas '9863-02' has a more bright red spathe. Additionally, 'ANTHDASYM' has a shorter spadix than '9863-02'.

'ANTHDASYM' differs from commercial variety 'ANTHOLODOJ' (U.S. Plant Pat. No. 20,254) in that 'ANTHDASYM' has non-touching lobes of the spathe and a long cordate leaf shape, whereas 'ANTHOLODOJ' has touching lobes of the spathe and a more broad cordate leaf shape. Additionally, the angle between spadix and peduncle of 'ANTHDASYM' is much larger than that of 'ANTHOLODOJ'.

'ANTHDASYM' differs from commercial variety 'ANTHCITOK' (unpatented) in that 'ANTHDASYM' has a dark red spathe, whereas 'ANTHCITOK' has a more bright red spathe. Additionally, the spadix length of 'ANTHDASYM' is shorter than that of 'ANTHCITOK' and the angle between spadix and peduncle of 'ANTHDASYM' is slightly smaller than that of 'ANTHCITOK'.

I claim:

1. A new and distinct variety of *Anthurium* plant named 'ANTHDASYM', substantially as illustrated and described herein.

* * * * *